United States Patent
Cho et al.

(10) Patent No.: US 7,580,178 B2
(45) Date of Patent: Aug. 25, 2009

(54) IMAGE-GUIDED MICROSURGERY SYSTEM AND METHOD

(75) Inventors: Gyoung Il Cho, Seoul (KR); Sang Hyune Baek, Suwon (KR); Cheong Soo Seo, Seongnam (KR)

(73) Assignees: Angstrom, Inc., Seongnam (KR); Stereo Display, Inc., Anaheim, CA (US)

( * ) Notice: Subject to any disclaimer, the term of this patent is extended or adjusted under 35 U.S.C. 154(b) by 326 days.

(21) Appl. No.: 11/300,205

(22) Filed: Dec. 13, 2005

(65) Prior Publication Data

US 2006/0092379 A1   May 4, 2006

Related U.S. Application Data

(63) Continuation-in-part of application No. 10/983,353, filed on Nov. 8, 2004, now Pat. No. 7,267,447, and a continuation-in-part of application No. 10/979,624, filed on Nov. 2, 2004, now Pat. No. 7,261,417, and a continuation-in-part of application No. 10/893,039, filed on Jul. 16, 2004, now Pat. No. 7,239,438, and a continuation-in-part of application No. 10/872,241, filed on Jun. 18, 2004, now Pat. No. 7,382,516, and a continuation-in-part of application No. 10/822,414, filed on Apr. 12, 2004, now Pat. No. 7,068,416, and a continuation-in-part of application No. 10/778,281, filed on Feb. 13, 2004, now Pat. No. 7,077,523.

(51) Int. Cl.
  *G02B 26/00* (2006.01)
  *G02B 26/08* (2006.01)
(52) U.S. Cl. .............. 359/291; 359/290; 359/295; 359/298
(58) Field of Classification Search ........... 359/290, 359/291, 295, 298, 225, 226, 625, 626, 846, 359/721, 627; 345/6
See application file for complete search history.

(56) References Cited

U.S. PATENT DOCUMENTS

| 2,002,376 A | 5/1935 | Mannheimer |
| 4,395,731 A | 7/1983 | Schoolman |
| 4,407,567 A | 10/1983 | Michelet |

(Continued)

FOREIGN PATENT DOCUMENTS

JP   08-043881   2/1996

(Continued)

OTHER PUBLICATIONS

Kanedo et al. 2000, "Quick Response Dynamic Focusing Lens using Multi-Layered Piezoelectric Bimorph Actuator," Procedding of SPIE vol. 4075:24-31.*

(Continued)

*Primary Examiner*—Scott J Sugarman
*Assistant Examiner*—Jack Dinh (57) ABSTRACT

The present invention provides an image-guided microsurgery system comprising a real-time three-dimensional microscopic imaging device and a three-dimensional display device. The imaging device generates an all-in-focus image or in-focus depthwise images with depth information in various fields of view, and the display device shows realistic three-dimensional images with features including reducing eye fatigue, watching by multiple viewers, two-dimensional/three-dimensional compatibility, color expression and high depth resolution, low manufacturing cost, and no significant data amount increase.

15 Claims, 10 Drawing Sheets

U.S. PATENT DOCUMENTS

| | | |
|---|---|---|
| 4,834,512 A | 5/1989 | Austin |
| 5,004,319 A | 4/1991 | Smither |
| 5,032,720 A | 7/1991 | White |
| 5,039,198 A | 8/1991 | VanBeek |
| 5,212,555 A | 5/1993 | Stoltz |
| 5,266,531 A | 11/1993 | Kikinis |
| 5,369,433 A | 11/1994 | Baldwin |
| 5,402,407 A | 3/1995 | Eguchi |
| 5,467,121 A | 11/1995 | Allcock |
| 5,612,736 A | 3/1997 | Vogeley |
| 5,696,619 A | 12/1997 | Knipe |
| 5,760,950 A | 6/1998 | Maly et al. |
| 5,785,651 A | 7/1998 | Kunn |
| 5,881,034 A | 3/1999 | Mano |
| 5,897,195 A | 4/1999 | Choate |
| 5,986,811 A | 11/1999 | Wohlstadter |
| 6,025,951 A | 2/2000 | Swart |
| 6,028,689 A | 2/2000 | Michalicek |
| 6,046,849 A | 4/2000 | Moseley et al. |
| 6,064,423 A | 5/2000 | Geng |
| 6,084,843 A | 7/2000 | Abe |
| 6,104,425 A | 8/2000 | Kanno |
| 6,111,900 A | 8/2000 | Suzudo |
| 6,123,985 A | 9/2000 | Robinson |
| 6,167,296 A | 12/2000 | Shahidi |
| 6,282,213 B1 | 8/2001 | Gutin |
| 6,315,423 B1 | 11/2001 | Yu |
| 6,329,737 B1 | 12/2001 | Jerman |
| 6,498,673 B1 | 12/2002 | Frigo |
| 6,507,366 B1 | 1/2003 | Lee |
| 6,549,730 B1 | 4/2003 | Hamada |
| 6,625,342 B2 | 9/2003 | Staple |
| 6,649,852 B2 | 11/2003 | Chason |
| 6,650,461 B2 | 11/2003 | Atobe |
| 6,658,208 B2 | 12/2003 | Watanabe |
| 6,711,319 B2 | 3/2004 | Hoen |
| 6,741,384 B1 | 5/2004 | Martin |
| 6,784,771 B1 | 8/2004 | Fan |
| 6,833,938 B2 | 12/2004 | Nishioka |
| 6,885,819 B2 | 4/2005 | Shinohara |
| 6,898,004 B2 | 5/2005 | Shimizu et al. |
| 6,900,901 B2 | 5/2005 | Harada |
| 6,900,922 B2 | 5/2005 | Aubuchon |
| 6,906,848 B2 | 6/2005 | Aubuchon |
| 6,906,849 B1 | 6/2005 | Mi |
| 6,914,712 B2 | 7/2005 | Kurosawa |
| 6,919,982 B2 | 7/2005 | Nimura |
| 6,929,369 B2 | 8/2005 | Jones |
| 6,934,072 B1 | 8/2005 | Kim |
| 6,934,073 B1 | 8/2005 | Kim |
| 6,943,950 B2 | 9/2005 | Lee |
| 6,958,777 B1 | 10/2005 | Pine |
| 6,970,284 B1 | 11/2005 | Kim |
| 6,995,909 B1 | 2/2006 | Hayashi |
| 6,999,226 B2 | 2/2006 | Kim |
| 7,023,466 B2 | 4/2006 | Favalora |
| 7,031,046 B2 | 4/2006 | Kim |
| 7,046,447 B2 | 5/2006 | Raber |
| 7,068,416 B2 | 6/2006 | Gim |
| 7,077,523 B2 | 7/2006 | Seo |
| 7,161,729 B2 | 1/2007 | Kim |
| 2002/0018407 A1 | 2/2002 | Komoto |
| 2002/0102102 A1 | 8/2002 | Watanabe |
| 2002/0135673 A1 | 9/2002 | Favalora |
| 2003/0058520 A1 | 3/2003 | Yu |
| 2003/0071125 A1 | 4/2003 | Yoo |
| 2003/0174234 A1 | 9/2003 | Kondo |
| 2003/0184843 A1 | 10/2003 | Moon |
| 2004/0009683 A1 | 1/2004 | Hiraoka |
| 2004/0012460 A1 | 1/2004 | Cho |
| 2004/0021802 A1 | 2/2004 | Yoshino |
| 2004/0052180 A1 | 3/2004 | Hong |
| 2004/0246362 A1 | 12/2004 | Konno |
| 2004/0252958 A1 | 12/2004 | Abu-Ageel |
| 2005/0024736 A1 | 2/2005 | Bakin |
| 2005/0057812 A1 | 3/2005 | Raber |
| 2005/0136663 A1 | 6/2005 | Terence Gan |
| 2005/0174625 A1 | 8/2005 | Huiber |
| 2005/0180019 A1 | 8/2005 | Cho |
| 2005/0212856 A1 | 9/2005 | Temple |
| 2005/0224695 A1 | 10/2005 | Mushika |
| 2005/0225884 A1 | 10/2005 | Gim |
| 2005/0231792 A1 | 10/2005 | Alain |
| 2005/0264870 A1 | 12/2005 | Kim |
| 2006/0012766 A1 | 1/2006 | Klosner |
| 2006/0012852 A1 | 1/2006 | Cho |
| 2006/0028709 A1 | 2/2006 | Cho |
| 2006/0187524 A1 | 8/2006 | Sandstrom |
| 2006/0209439 A1 | 9/2006 | Cho |

FOREIGN PATENT DOCUMENTS

| | | |
|---|---|---|
| JP | 11-069209 | 3/1999 |
| JP | 2002-288873 | 10/2002 |

OTHER PUBLICATIONS

Cho, 2003, "Fast-response Variable Focusing Micromirror Array Lens," Procedding of SPIE vol. 5055: 278-286.*

* cited by examiner

IMAGE-GUIDED MICROSURGERY SYSTEM AND METHOD

REFERENCES TO RELATED APPLICATIONS

This application is a continuation-in-part of, and claims priority to U.S. patent application Ser. No. 10/778,281 filed Feb. 13, 2004, U.S. patent application Ser. No. 10/822,414 filed Apr. 12, 2004, and U.S. patent application Ser. No. 10/979,624 filed Nov. 2, 2004, U.S. patent application Ser. No. 10/983,353 filed Nov. 8, 2004, U.S. patent application Ser. No. 10/872,241 filed Jun. 18, 2004, U.S. patent application Ser. No. 10/893,039 filed Jul. 16, 2004, all of which are hereby incorporated by reference.

FIELD OF INVENTION

The present invention relates to microsurgery systems, and in particular, an image-guided microsurgery system comprising a real-time three-dimensional imaging device and a three-dimensional display device.

BACKGROUND OF INVENTION

Microsurgery includes any operation that uses visual magnification of a target structure to enhance the performance of a procedure, in which surgical microscopes are a primary vision system. Thanks to its minimal invasiveness, less trauma, less postoperative pain, and fast recovery, the microsurgery is widely used in various fields such as neurosurgery, reconstructive surgery, peripheral vascular surgery, and ophthalmology.

Three-dimensional vision provides more informative and intuitive observation of scene and precise interaction with environment than monocular vision does. Since microsurgery requires extremely precise hand-eye coordination and minute manipulation, three-dimensional microscopic vision system becomes indispensable element in microsurgery. A simple surgical binocular microscope comes with a pair of microscope eyepieces that provides binocular parallax and has been widely used for a long time. However, it can cause eye-strain, fatigue, and back and cervical pain for prolonged uses. Three-dimensional display devices can make these problems avoided.

Further, conventional microscopes have a low axial resolution, or a short depth of field, which generate blurred images in out-of-focus area. Microsurgery requires high resolution images in both lateral and axial directions. Confocal microscopes (U.S. Pat. No. 5,032,720) can satisfy these requirements and also provide depth information, in which a point of interest is illuminated by a point source of light using a pinhole aperture. Typically, this type of microscopes first scans an object point by point, and integrates this information to generate a complete image using an image processing system. Due to the complicated procedure, a slow imaging process is unavoidable in confocal microscopes. Further, they tend to have bulky and complicated structures.

Majority of three-dimensional display systems use the binocular parallax phenomena as well. Two images that are taken from two microscopes equipped with imaging systems (i.e. cameras) at the same time in different viewing angles are displayed in a three-dimensional display system. In a stereoscopic display system, these images are displayed in turns with a fast refresh rate. Three-dimensional images can be seen using a head mounted LCD shutter device or an overhead monitor through polarized glasses. These special eye-wears can cause discomfort and image degrading effect such as image flickering and low brightness. In an autostereoscopic display system, stereoscopic images are displayed simultaneously by dividing a two-dimensional display into two sets of pixels. Using parallax barriers, they create windows, in which each eye can see an only intended image. Autostereoscopic device does not require a special eye-wear but there are limits on the viewing angle and range.

In the image-guided surgery, preoperative medical images from multiple imaging devices such as magnetic resonance imaging (MRI), computer tomography (CT), ultrasound, and angiography, are employed in both diagnosis and treatment. These images reveal anatomical abnormalities such as tumors, infection, sclerosis, torn ligament, and osteoporosis as well as other anatomical structures in two-dimensional sectional or three-dimensional volumetric view.

To maximize accessibility and usability of these preoperative images during an operation, these images are registered with each other, with patient, with tracking instrument, and with intraoperative real-time microscope video image. Through the registration process, some of preoperative images and intraoperative video images are overlapped and displayed together so that a surgeon can observe underlying structures as well as surface structures during the operation, which can prevent unnecessary damages on the normal structures.

Registering a preoperative image with intraoperative stereoscopic video images and displaying them together in the stereoscopic display devices can be complicated because the preoperative image needs to be transformed into the data format that stereoscopic display devices require. Also, the transformation from a three-dimensional volumetric image to two-dimensional flat images can cause loss of valuable information.

There exist other types of three-dimensional display systems. Holography is a three-dimensional display method that generates a real image in the space (U.S. Pat. No. 5,266,531). Holography has been used for three-dimensional image display very limitedly due to its technical complexity and high manufacturing cost.

U.S. Pat. No. 4,834,512 to Austin discloses a three-dimensional display having a dimensional display, a fluid-filled variable focal length lens, and control device for manipulating the display and the lens. The two-dimensional display sequentially presents two-dimensional images that represent the cross sections of an object at different image depths. The fluid-filled variable focal length lens is disposed in front of the two-dimensional display and has a membrane that responds to the pressure of the fluid within the lens. Austin's display has a disadvantage that the display is unsuitable for displaying realistic three-dimensional images because the focus changing speed of the fluid-filled lens is slow.

U.S. Pat. No. 5,986,811 to Wohlstadter discloses an imaging method and system for creating three-dimensional image from a two-dimensional image having a plurality of image points. The imaging system includes an array of micro-lenses having variable focusing length, and means for holding the micro-lenses in alignment with the image points of the two-dimensional display.

A new image-guided microsurgery system comprising a imaging and a display system must satisfy current demands including providing three-dimensional image with a variable field of view, reducing eye fatigue, watching by multiple viewers, two-dimensional/three-dimensional compatibility, color expression and resolution that equal to or exceed those of HDTV, low manufacturing cost, and no significant data amount increase.

SUMMARY OF INVENTION

The present invention provides an image-guided microsurgery system comprising a real-time three-dimensional microscopic imaging device and a three-dimensional display device using a variable focal length micromirror array lens (MMAL).

An objective of the invention is to provide a real-time three-dimensional microscopic imaging device that provides intraoperative in-focus depthwise images with depth information of each depthwise image or an intraoperative all-in-focus image with depth information of each pixel.

The real-time three-dimensional microscopic imaging device comprises at least one camera system having a lens system including variable focal length lenses, an objective lens, and auxiliary lenses, an imaging unit, and an image processing unit.

The variable focal length lens comprises a micromirror array lens. The variable focal length MMAL includes many micromirrors. The following U.S. patents and applications describe the micromirror array lens: U.S. Pat. No. 6,934,072 to Kim, U.S. Pat. No. 6,934,073 to Kim, U.S. patent application Ser. No. 10/855,554 filed May 27, 2004, U.S. patent application Ser. No. 10/855,715 filed May 27, 2004, U.S. patent application Ser. No. 10/857,714 filed May 28, 2004, U.S. patent application Ser. No. 10/857,280 filed May 28, 2004, U.S. patent application Ser. No. 10/893,039 filed May. 28, 2004, U.S. patent application Ser. No. 10/983,353 filed Mar. 4, 2005, all of which are hereby incorporated by reference.

The micromirror array lens is suitable for the three dimensional imaging and display device of the present invention since it has a fast focus change speed, large range of focal length, and since it can be made to have a small or large aperture.

The imaging unit includes one or more two-dimensional image sensors taking an original two-dimensional image at each focal plane. The detail for three dimensional imaging using MMAL can be found in U.S. patent application Ser. No. 10/822,414 filed Apr. 12, 2004, U.S. patent application Ser. No. 10/979,624 filed Nov. 2, 2004, and U.S. patent application Ser. No. 11/208,115 filed Aug. 19, 2005.

The image sensor takes two-dimensional images with different focal planes that are shifted by changing the focal length of the variable focal length MMAL. The image processing unit extracts in-focus pixels or areas from original images at different focal planes to generate in-focus depthwise images or an all-in-focus image. Based on the known focal length and the known distance from the lens to the image, depth information of each depthwise image relative to the imaging device can be obtained. There are several methods for the image processing unit to obtain an all-in-focus image. Recent advances in both the image sensor and the image processing unit make them as fast as they are required to be. Depth information of each pixel of the all-in-focus image can be obtained in the same way as in the depthwise image case.

The present invention includes a three-dimensional display device, which displays the images taken by three dimensional imaging unit, as explained below. Three-dimensional display using the MMAL is proposed in the U.S. patent application Ser. No. 10/778,281 filed Feb. 13, 2004 and U.S. patent application Ser. No. 10/979,624 filed Nov. 2, 2004.

Depthwise images or all-in-focus images can be displayed by various three-dimensional display devices through geometric data transformation. All the processes are achieved within a unit time which is at least persistent rate of the human eye. Unlike conventional stereo vision systems that require at least two camera systems, the current invention can determine the three-dimensional information using only a single camera system with a fast response time, and this renders a simpler camera calibration and a more compact imaging device.

Another objective of the invention is to provide the imaging device with a variable field of view in order to allow a microscopic observation. It is efficient and desirable to use a wide field of view with lower resolution images for viewing an overall internal structures and spotting an area of interest, and a narrow field of view with higher resolution images for diagnosis and treatment. The variable focal length MMAL of the present invention has a large range of focal length variation, which can offer a variable field of view; a shorter focal length for a wider field of view and a longer focal length for a narrow field of view. The size of field of view is changed without a macroscopic servo mechanism because each micromirror of the variable focal length MMAL is actuated by the electrostatic force and/or electromagnetic force.

The real-time three-dimensional microscopic imaging device of the present invention has the following advantages: (1) the device can make a real-time three-dimensional image including intraoperative in-focus depthwise images and an intraoperative all-in-focus image; (2) the device has a large range of depth; (3) the device has a high optical efficiency; (4) the device can have high depth resolution; (5) the device has a variable field of view; (6) the cost is inexpensive because the micromirror array lens is inexpensive; (7) the device has a very simple structure because there is no macroscopic mechanical displacement or deformation of the micromirror array lens; (8) the device is compact; (9) the device requires small power consumption when the micromirror array lens is actuated by electrostatic force.

Other objectives of the invention are to provide a three-dimensional display device that has a simple construction and realistic image representation, to provide a three-dimensional display device and method that utilize a set of depthwise images, to provide a three-dimensional display device that can display a large range of image depth, to provide a three-dimensional display device that provides two-dimensional/three-dimensional compatibility, and to provide a three-dimensional display device that provides a large image size.

The three-dimensional image display device of the present invention has the following advantages: (1) since the three-dimensional display device actually generates three-dimensional images in the space, the device does not suffer from the disadvantage of prior art device using parallax including imaging difficulties due to considerations for arbitrary distribution of the viewer's position, and binocular disparity due to deviations in the distance between the two eyes, vergence, accommodation, watching by more than one viewers, and the relative position change of the three-dimensional image due to viewer's movement; (2) the cost for providing three-dimensional image data is inexpensive since the data needs only depth information in addition to two-dimensional image information, and thus there is no significant increase in data amount; (3) intraoperative image and preoperative images can be displayed simultaneously; and (4) the device can be easily converted to a two-dimensional display and vice versa.

Although the present invention is briefly summarized herein, the full understanding of the invention can be obtained by the following drawings, detailed description, and appended claims.

DETAILED DESCRITION OF THE ILLUSTRATED EMBODIMENTS

Figure 1:
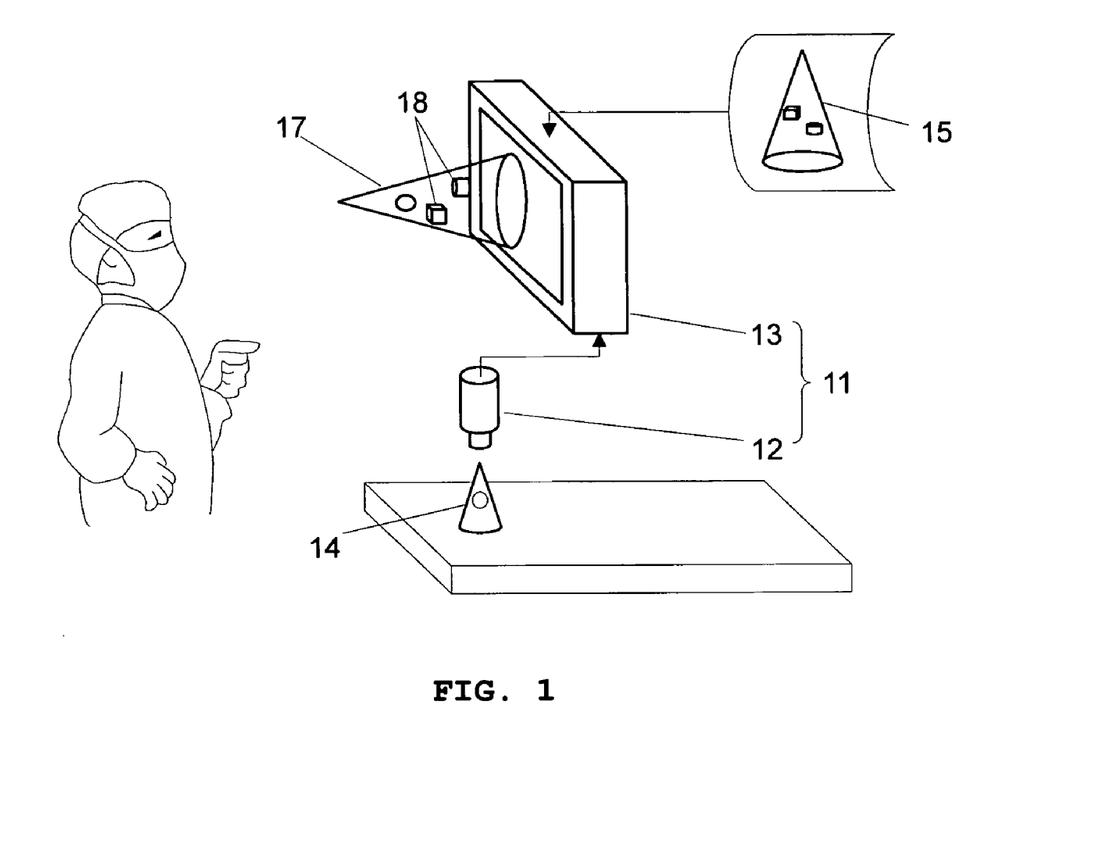
FIG. 1 is a schematic illustration of an image-guide microsurgery system.

FIG. 1 illustrates an image-guide microsurgery system 11 comprising a real-time three-dimensional microscopic imaging device 12 and a three-dimensional display device 13. The imaging device 12 comprises a variable focal length MMAL or MMAL's, an imaging unit, and an image processing unit. A microscope system can be embodied to have the magnified images of anatomical structures. The imaging unit (not shown) of the imaging device 12 receives two-dimensional images with different focal planes that are shifted by changing the focal length of the variable focal length MMAL. The image processing unit extracts in-focus pixels or areas from original pictures at different focal planes to generate intraoperative depthwise images or an intraoperative all-in-focus image, and calculates three-dimensional position data of the anatomical structures 14 with respect to the image coordinate system. The imaging device 12 is communicatively connected to the three-dimensional display device 13.

The three-dimensional display 13 forms three-dimensional images by using all-in-focus image from the imaging device 12 and preoperative images 15 from a storage space simultaneously after registering one image with the other. The combined image 17 shows underlying anatomical structures 18 as well as surface structures.

Figure 2:
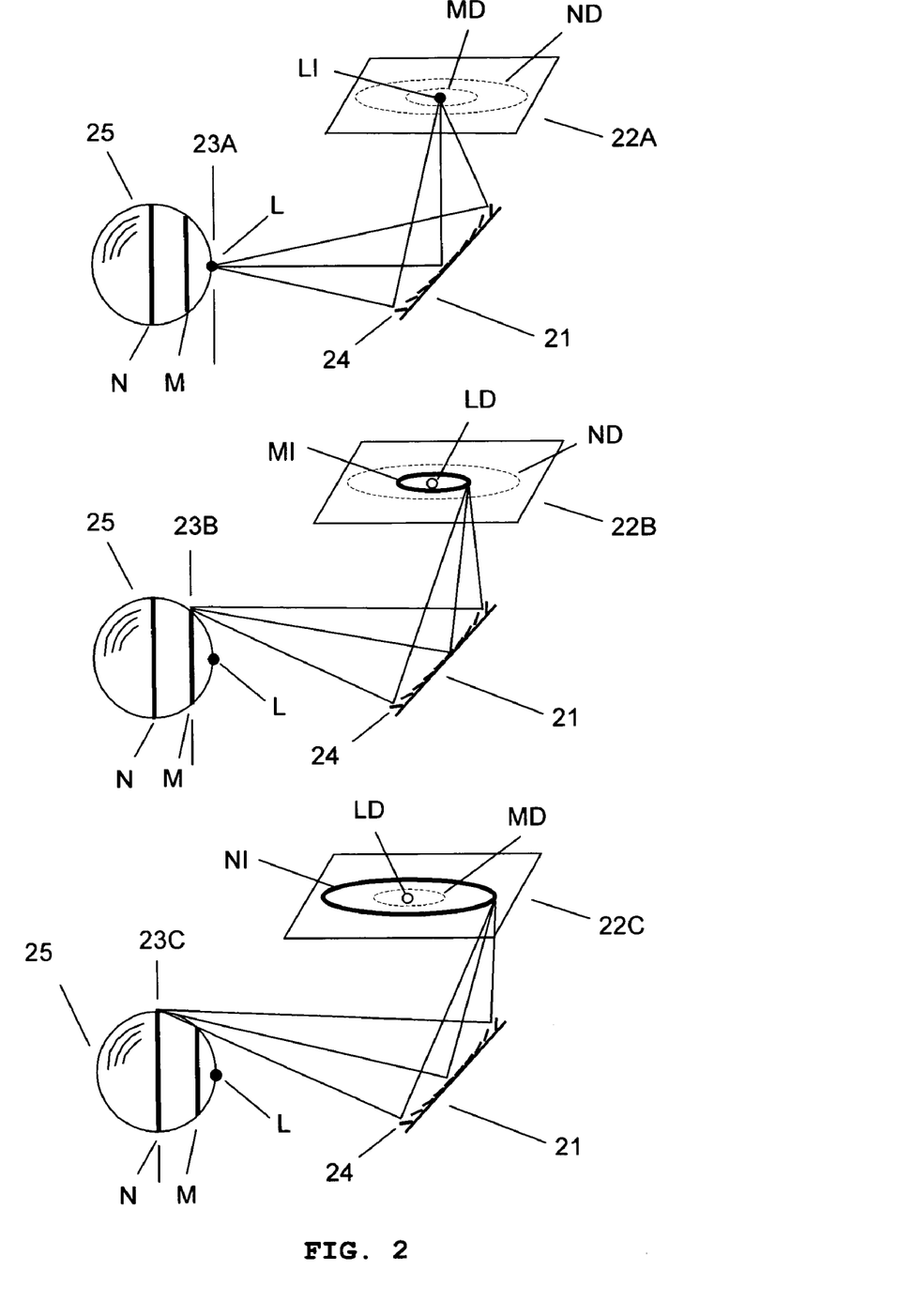
FIG. 2 is a schematic diagram showing how a three-dimensional image is obtained from two-dimensional images with different focal planes changing the focal length of the MMAL.

FIG. 2 shows how a MMAL 21 takes two-dimensional images 22A, 22B, 22C with the focal planes 23A, 23B, 23C changing the focal length of the MMAL 21. The MMAL 21 comprises a plurality of micromirrors 24. Each micromirror 24 is controlled to change the focal length of the variable focal length MMAL 21. The focal length of the MMAL 21 is changed by rotation and translation of each micromirror 24 by electrostatic and/or electromagnetic force. Two-dimensional images 22A, 22B, 22C are taken with the depth information which corresponds to the position of the focal plane. The two-dimensional image 22A has in-focus image LI at the focal plane 23A, which is the image of the portion L of an object 25. Images MD, ND of portion M, N of an object 25 are defocused. The image processing unit determines the in-focus pixels LI from the two-dimensional images 22A. The two-dimensional image 22A with depth information gives in-focus pixels LI corresponding to the focal plane 23A. The two-dimensional images 22B, 22C with the second and third focal plane 23B, 23C are processed in the same manner as the first focal plane 23A to get in-focus images with depth information. The variable focal length MMAL is also an adaptive optical component compensating the aberration of the imaging system.

Figure 3:
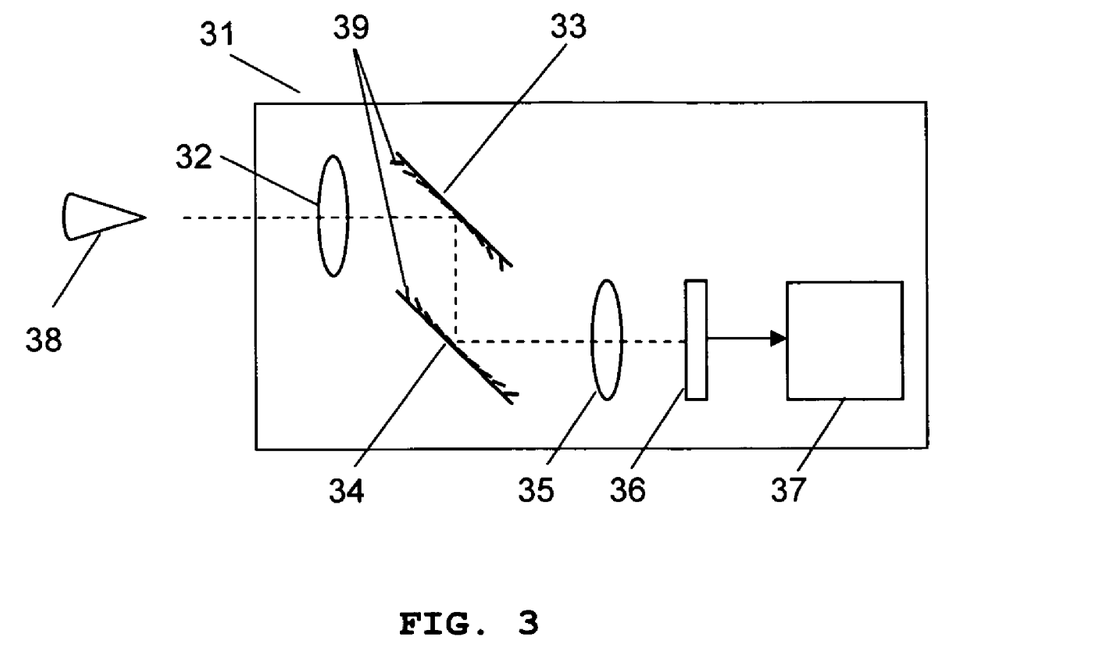
FIG. 3 illustrates a real-time three-dimensional microscopic imaging device providing a variable magnification of the object (variable field of view)

FIG. 3 illustrates a real-time three-dimensional microscopic imaging device 31 providing a variable magnification of the object (variable field of view). The real-time three-dimensional microscopic imaging device 31 comprises a lens system 32, 33, 34, 35, an imaging unit 36, and an image processing unit 37. The lens system includes an objective lens 32, and a variable focal length MMAL 33 optically coupled to the objective lens 32, configured to change the focal plane by changing the focal length of the MMAL 33. The lens system also comprises an auxiliary lens 32, 35 or group of lenses to change the field of view and the image resolution. Also the lens system comprises one or more auxiliary lenses for increasing the numerical aperture of the imaging system.

The lens system can comprise the second variable focal length MMAL 34 for variable magnification of the object 38. The focal length of the first variable focal length MMAL 33 is controlled to change the magnification of the object 38 (size of field of view), wherein the image of an object 38 is optically magnified. The focal length of the second variable focal length MMAL 34 is controlled to change the focal plane to take in-focus depthwise images. The objective lens 32 and the auxiliary lens 35 provide additional magnification. The field of view is adjusted without the macroscopic movement of the lens system or time delay since each micromirror 39 of the variable focal length MMAL's 33 and 34 is actuated by electrostatic and/or electromagnetic force. The image processing unit 37 generates all-in-focus image with depth information from the two dimensional images in the imaging unit 36 with depth information form the variable focal length MMAL 33. The variable focal length MMAL 33 and 34 changes their focal lengths so fast that the imaging processes are achieved faster than the persistence rate of the human eye.

FIGS. 4A-4D illustrate the general principle regarding the distance or depth of an image formed by a lens and the focal length of the lens. When the light from an object passes through a lens, it converges or diverges depending on the distance L between the object and the lens, and the focal length of the lens. In the description of the present invention, a lens means an optical element that focuses light, and is not confined to a refractive type lens.

FIGS. 4A-4D demonstrate that the position of a virtual or real image changes according to the focal length of a lens, and the position of the image will change continuously as the focal length varies continuously.

Figure 4A:
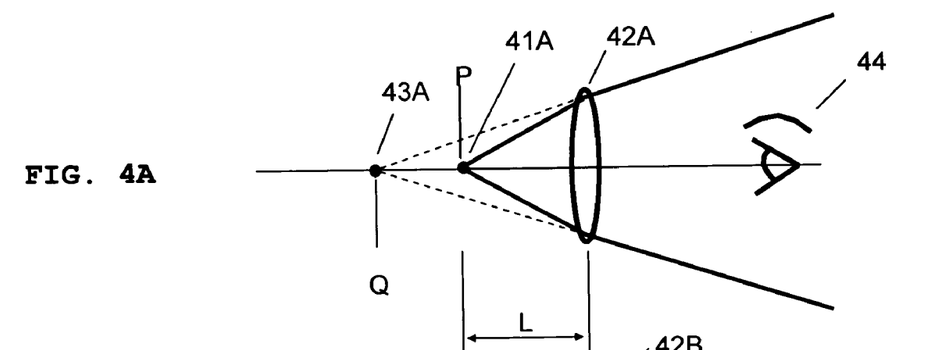
FIGS. 4A-4D are schematic diagrams showing how the depth of an image is changed as the focal length of a lens is changed.
Figure 4B:
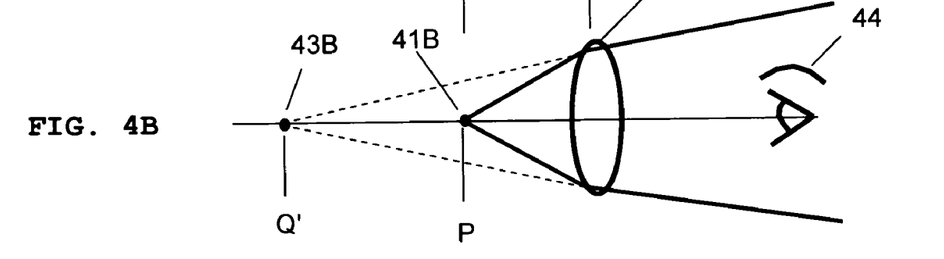

FIG. 4A shows that the light from an object 41A passes through a lens 42A and then diverges with a different angle. FIG. 4B is a similar diagram for a lens 42B having a shorter focal length. The light refracted by the lens 42A, 42B forms a virtual image 43A, 43B. When a viewer 44 sees the refracted light, the viewer perceives the object 41A, 41B, which are positioned at point P, as existing at point Q, Q'.

Figure 4C:
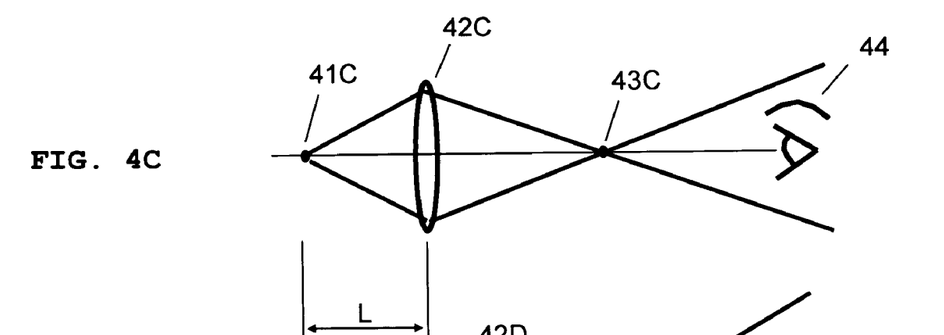
Figure 4D:
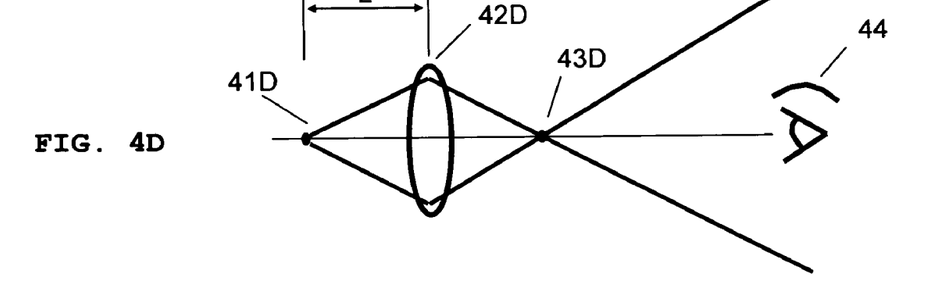

FIG. 4C shows that the light from an object 41C passes through a lens 42C and then converges to form a real image 43C. FIG. 4D is a similar diagram for a lens 42D having a shorter focal length. When the viewer 44 sees an object 41C, 41D through the lens 42C, 42D, the viewer perceives the object 41C, 41D as the real image 43C, 43D.

For a given distance L between the object and the lens, the position of the image formed by the lens varies depending on the focal length of the lens. The position of the image can be calculated with Gaussian lens formula. FIGS. 4A and 4B show that the virtual image 43A is nearer to the viewer 44 with the lens 42A having a longer focal length, and the virtual image 43B is farther from the viewer 44 with the lens 42B having a shorter focal length. FIGS. 4C and 4D show that the real image 43C is nearer to the viewer 44 with the lens 42C having a longer focal length, and the real image 43D is farther from the viewer 44 with the lens 42D having a shorter focal length.

Figure 5:
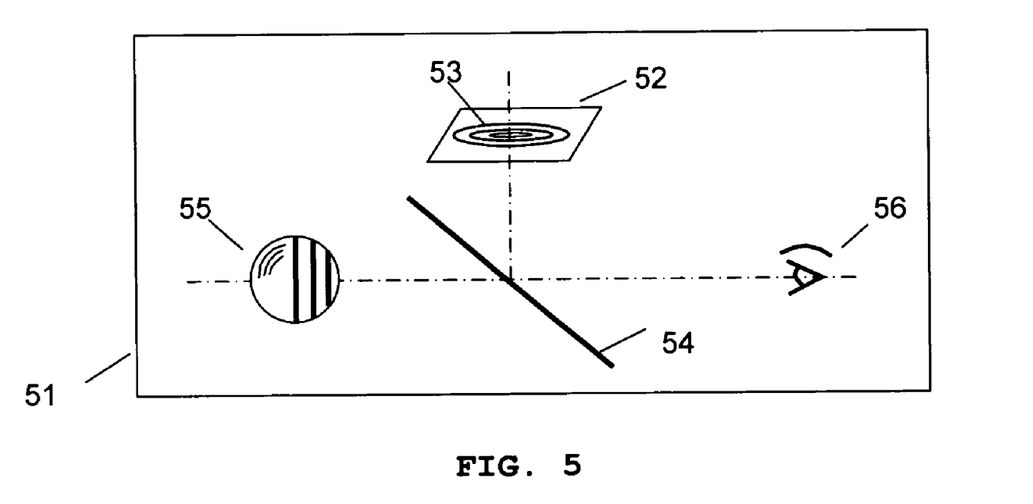
FIG. 5 is a schematic diagram showing a three-dimensional display device of the present invention.

FIG. 5 schematically shows a three-dimensional display device 51 according to the first embodiment of the present invention. The three-dimensional display device 51 includes a two-dimensional display 52 displaying a depthwise sectional two-dimensional image 53 at a time with corresponding depth information, and a variable focal length MMAL 54 receiving light from the two-dimensional display 52 and forming a three-dimensional image 55. The three-dimensional display 51 forms three-dimensional image from the all-in-focus image with depth information. The all-in-focus images comprises corresponding depthwise images, in which each of the depthwise image represents the portion of the all-in-focus image having the same image depth. The variable focal length MMAL 54 changes its focal length so that the all-in-focus image with depth information 55 looks like three-dimensional one for a viewer 56 of the three-dimensional display device 51.

A three-dimensional image is generated in the space by displaying depthwise two-dimensional images on corresponding depths in the space with the variable focal length MMAL. The two-dimensional display shows only pixels that should be imaged at the same depth at a given moment or a given frame, and the variable focal length MMAL adjusts its focal length in order to image the depthwise image to the required location in the space.

Figure 6A:
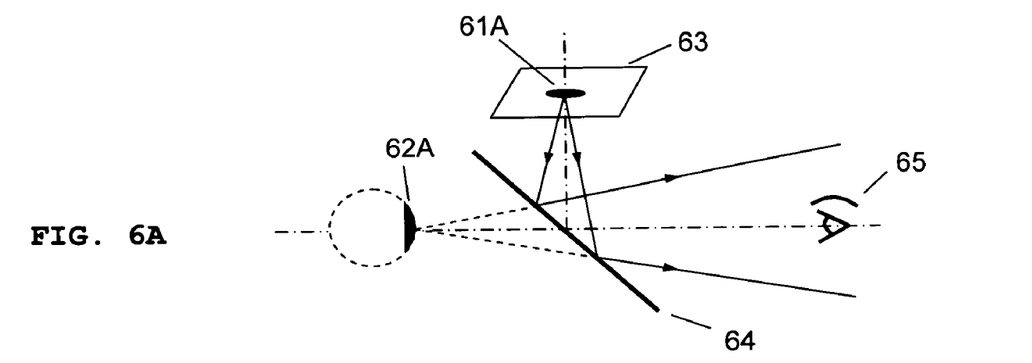
FIGS. 6A-6C are schematic diagrams showing how two-dimensional display and variable focal length MMAL displays the three-dimensional images.
Figure 6B:
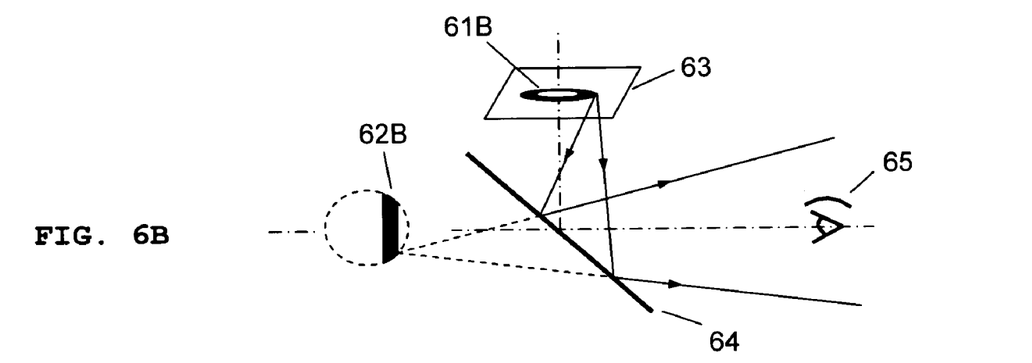
Figure 6C:
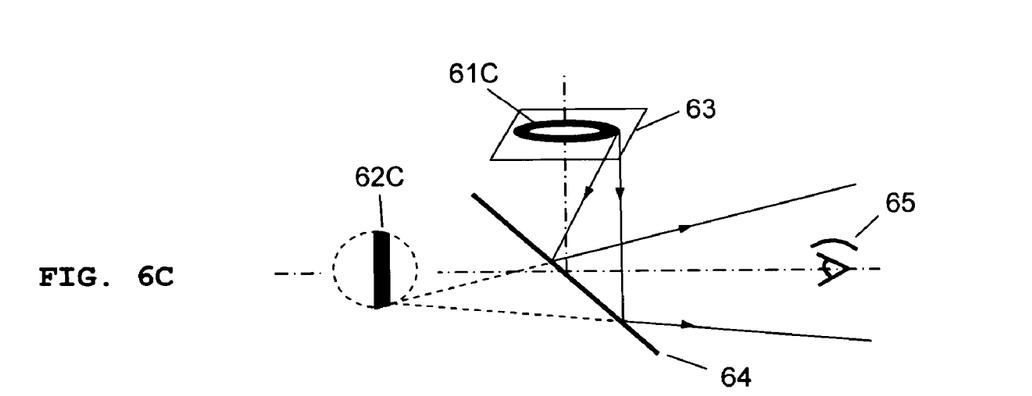

FIGS. 6A-6C show that the depthwise sectional two-dimensional image includes a predetermined depth number of depthwise sectional images 61A, 61B, 61C that are displayed within a unit time, and the all-in-focus image with depth information includes corresponding three-dimensional images with depth information 62A, 62B, 62C. Each of the depthwise sectional images 61A, 61B, 61C represents the portion of the depthwise sectional image having the same image depth. The two-dimensional display 63 displays one depthwise sectional image at a time. The focusing speed of the variable focal length MMAL 64 is at least equal to the product of the persistent rate of the human eye and the number of depths so that the all-in-focus image with depth information looks three-dimensional to the viewer 65.

In order that the sequentially displayed all-in-focus images with depth information look as the three-dimensional secondary image to the viewer 65, the all-in-focus images with depth information must be displayed fast enough to utilize human eye's afterimage effect. That is, the variable focal length MMAL 64 must be able to change its focal length fast enough.

For example, to display a three-dimensional image, the images should be displayed at least persistent rate of the human eye. In order to display a three-dimensional image having 10 image depths, since the depths must all be displayed within one thirtieth of a second, a variable focusing speed and two-dimensional display speed of at least about 300 Hz (30×10 Hz) is required.

The number of image depths varies depending on the structure and capability of a two-dimensional display device, and increases for a better image quality.

The variable focal length MMAL 64 is made of many micromirrors. The MMAL is synchronized with the two-dimensional display 63 to display the all-in-focus images with depth information 62A, 62B, 62C according to the depths of the two-dimensional depthwise sectional images 61A, 61B, 61C. To display the all-in-focus image with depth information, which has continuous depths, the focal length of the MMAL is synchronized with the depths of the two-dimensional depthwise sectional images 61A, 61B, 61C, and thus continuously changes. In order that the all-in-focus image with depth information should be displayed realistically, speed of focal length change of lens and that of two-dimensional display 63 must be equal or greater than the product of the persistent rate of the human eye and the number of the depthwise images.

Figures 7A, 7B:
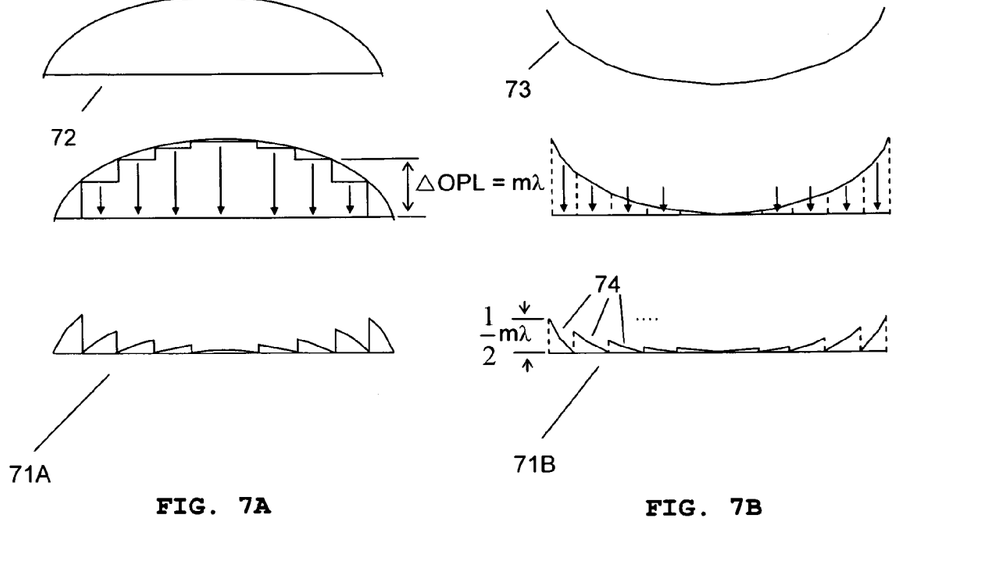
FIG. 7A is a schematic diagram showing how a refractive Fresnel lens replaces an ordinary single-bodied lens.
FIG. 7B is a schematic diagram showing how a reflective Fresnel lens replaces an ordinary single-bodied mirror.

FIG. 7A schematically shows how a refractive Fresnel lens 71A replaces an ordinary single-bodied lens 72. FIG. 7B shows how a reflective Fresnel lens 71B, replacing an ordinary single-bodied mirror 73, is formed with micromirror array lens. The micromirror array lens includes a plurality of micromirrors 74, and each micromirror 74 is controlled to form a reflective Fresnel lens 71B and to change the focal length of the lens.

In order to obtain a bright and sharp image, the variable focal length MMAL must meet the two conditions for forming a lens. One is that all the rays should be converged into the focus. And the other is that the phase of the converged rays must be the same. Even though the rays have different optical path lengths, same phase condition can be satisfied by adjusting the optical path length difference to be integer multiples of the wavelength of the light. Each facet converges rays to one point and rays refracted or reflected by different facets have an optical path length difference of integer multiples of the incident light.

To change the focal length of the MMAL, the translational motion and/or the rotational motion of each of the micromirrors are controlled to change the direction of light and to satisfy the phase condition of the light.

Figure 8A:
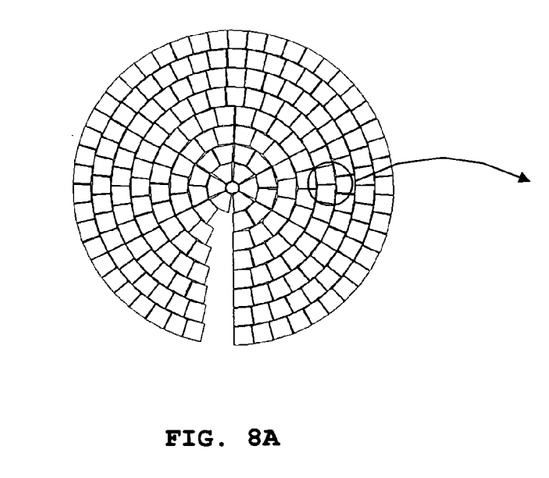
FIG. 8A is a schematic plan view showing a variable focal length MMAL that is made of many micromirrors.
Figure 8B:
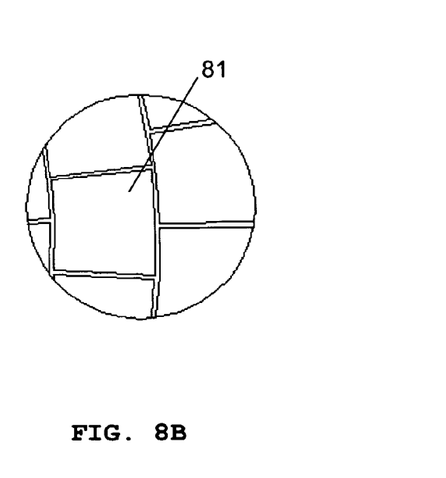
FIG. 8B is an enlarged detail plan view of the micromirrors.

FIGS. 8A and 8B show that the micromirrors 81 are arranged to form many concentric circles. The micromirrors 81 are arranged in a flat plane as shown in FIG. 7B.

The variable focal length MMAL must meet the following requirements to be used in three-dimensional display and imaging system. First, it must have a focal length change speed fast enough for three-dimensional display. Second, it must have a large range of numerical aperture change, since the depth range that can be imaged depends on the range of numerical aperture change. Third, it needs to have a large diameter depending on constructions of three-dimensional displays.

The MMAL meets three requirements. First, the response speed of the micromirror 81 exceeds the persistent rate of the human eyes times the number of depths. Therefore, it is possible to make the focal length change within hundreds of micro-seconds.

The range of numerical aperture change of the MMAL is large. Therefore, as explained above, the micromirror array lens has a greater range of image depths, which is an essential requirement for a three-dimensional display.

In contrast with a lens having a continuous shape, for which it becomes difficult to make an ideal curved surface as the size becomes larger, there is no difficulty in enlarging the size of MMAL, since the MMAL consists of discrete micromirrors.

Since the MMAL a reflective lens, the optical system of the three-dimensional display device cannot be aligned in a line. An optical arrangement, in which the reflected light is not blocked by the two-dimensional display, is required.

Figure 9:
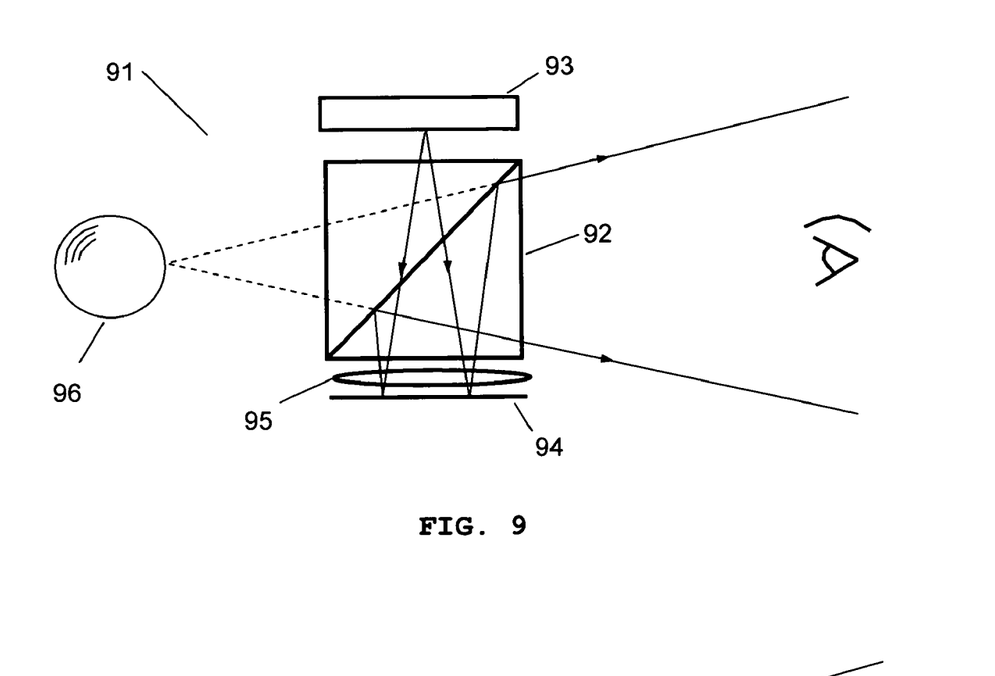
FIG. 9 is a schematic diagram showing a beam splitter and an auxiliary lens added to the three-dimensional display device.

FIG. 9 shows an arrangement in which the three-dimensional display device 91 further includes a beam splitter 92 positioned in the path of light between a two-dimensional display 93 and a variable focal length MMAL 94. The two-dimensional display 93 and the variable focal length MMAL 94 are arranged parallel with each other. The beam splitter 92 changes the direction of the light by 90°, and thus simulating an in line optical arrangement. The MMAL is positioned perpendicular to the light path.

Alternatively, referring back to FIG. 5, the variable focal length MMAL 54 is positioned so that the path of the light reflected by the variable focal length MMAL 54 is not blocked by the two-dimensional display 51. The arrangement in FIG. 5 has advantages of simple structure and wider field of view since the distance between the two-dimensional display and the variable focal length MMAL 54 is closer than that of the arrangement with the beam splitter 92. However, it needs special consideration of the correction of the aberration induced by the obliquely positioned variable focal length MMAL 54. The choice of either arrangement depends on the use of the display device.

As shown in FIG. 9, the three-dimensional display device may further include an auxiliary lens 95 having a predetermined focal length and positioned adjacent to the variable focal length MMAL 94. The all-in-focus image with depth information 96 is formed by the effective focal length of the variable focal length MMAL 93 and the auxiliary lens 95. With the auxiliary lens 95, the variable focusing range of the three-dimensional display device can be extended or changed to a desired range. A refractive type Fresnel can be used as an auxiliary lens 95.

Figure 10:
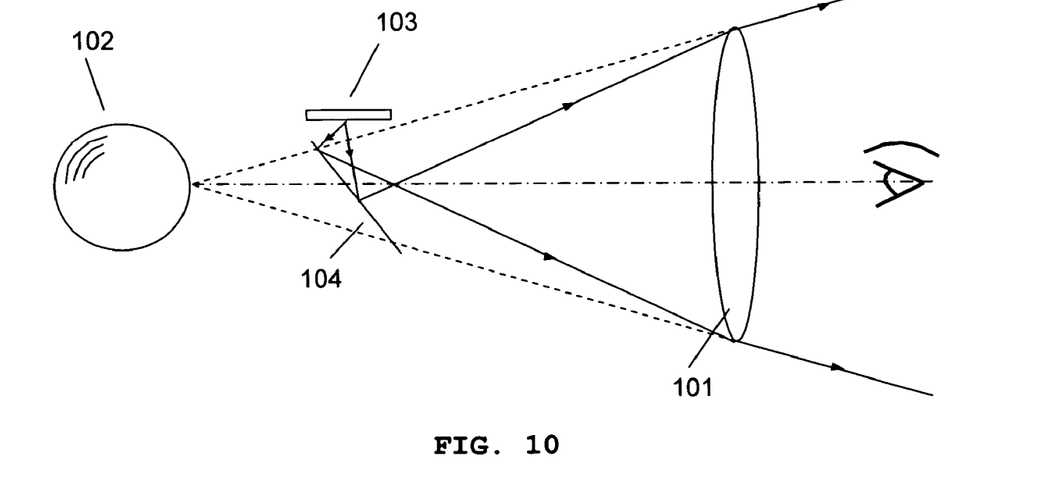
FIG. 10 is a schematic diagram showing a magnifying lens added to the three-dimensional display device.

As shown in FIGS. 5 and 9, the variable focal length MMAL's 54, 94 should have the size of the screen. For a device having a large display screen, it is almost impossible or extremely expensive to make a variable focal length MMAL having a size as large as that of the screen. FIG 10 shows that the three-dimensional display device may further include an auxiliary lens 101 that magnifies the all-in-focus image with depth information 102, in order to overcome the limitation of size. The auxiliary lens 101 may be an ordinary refractive lens or a refractive Fresnel lens. The screen size becomes the size of the auxiliary lens 101, which has a fixed focal length. A two-dimensional display 103 and a variable focal length MMAL 104 can have a compact size that is much smaller than the size of the auxiliary lens 101. The effective focal length of the three-dimensional display device is varied by changing the focal length of the variable focal lens 104.

The focal length of the variable focal length MMAL may be controlled to be fixed. By fixing the focal length of the variable focusing length and operating the two-dimensional display as a general two-dimensional display device, the three-dimensional display device can be easily converted into a two-dimensional display device.

Method for displaying a three-dimensional image may be one using a virtual image as illustrated in FIGS. 4A and 4B, or one using a real image as illustrated in FIGS. 4C and 4D. The method using a real image has an advantage that it enables more realistic display since the image is generated closer to the viewer, and has a disadvantage that the range of display is limited between the viewer and the screen. With the method using a virtual image, the image is generated behind the screen. This method has an advantage that it can display an image having depth ranging from the screen to the infinity.

Figure 11A:
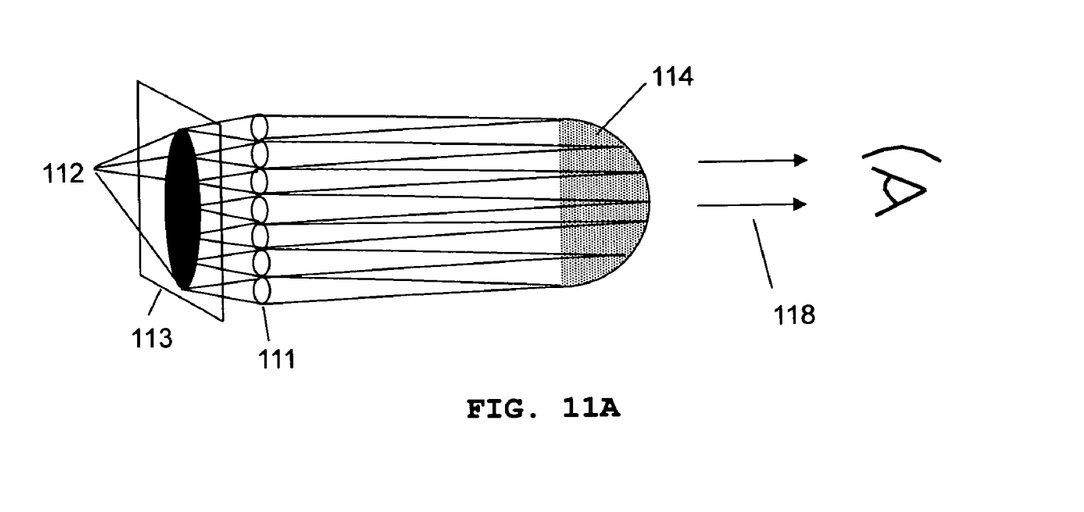
FIG 11A is a schematic diagram showing a three-dimensional display device, which has variable focal length MMAL corresponding to pixels of a two-dimensional display.
Figure 11B:
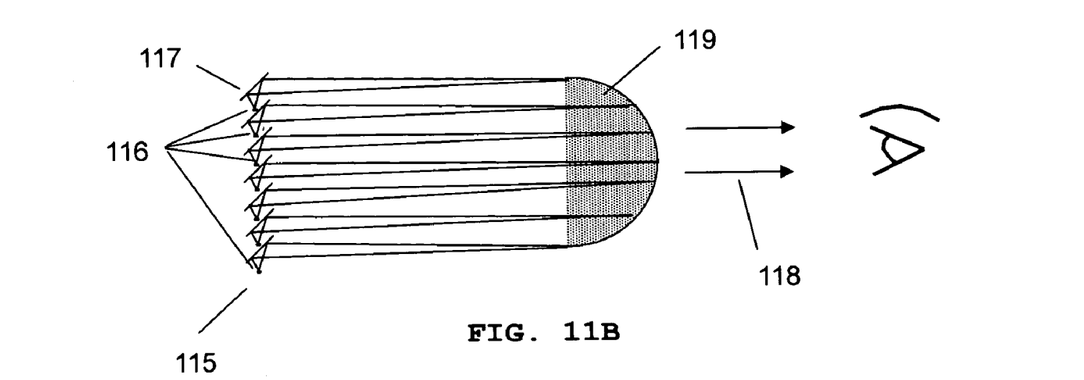
FIG 11B is a schematic diagram showing that micromirror array lens is used as the variable focal length MMAL for the device of FIG. 11A.

FIGS. 11A and 11B show a second embodiment of the present invention. FIG. 11A shows how a three-dimensional display device, which has many variable focal length MMAL's 111 corresponding to pixels 112 of a two-dimensional display 113, operates to display a three-dimensional image 114. The partial image displayed by each pixel 112 is imaged at its image depth by the variable focal length MMAL 111 corresponding to the pixel 112. Since the partial image displayed by each pixel is individually handled by the corresponding variable focal length MMAL, dividing an image into depthwise images and displaying the depthwise images are not required, and thus this embodiment does not need a high speed two-dimensional display and a high speed variable focal length MMAL. A two-dimensional display having a usual speed can be used. The size of the variable focal length MMAL 111 is similar to that of the pixel 112.

FIG. 11B shows schematically a three-dimensional display device 115. The three-dimensional display device 115 includes a two-dimensional display having a plurality of pixels 116, and a plurality of variable focal length MMAL's 117. Each of the variable focal length MMAL 117 corresponds to each of the pixel 116. The focusing speed of the variable focal length MMAL 117 is at least persistent rate the human eye, and each of the variable focal length MMAL 117 reflect light from the two-dimensional display. The focal length of each of the variable focal length MMAL 117 changes according to the image depth of an image displayed by each of the pixels 116. Each of the variable focal length MMAL 117 is made of a MMAL.

Since the MMAL is a reflective optical element, the lens element 117 is positioned so that the reflected light is not blocked by the two-dimensional display. Each of the pixels 116 displays a portion of a depthwise sectional image in a direction orthogonal with the device display direction 118 of the three-dimensional display device 115. Each of the lens elements 117 is positioned at an angle of 45° with respect to the display direction of the pixels 116 and the device display direction 118. An all-in-focus image with depth information 119, which is three-dimensional, is formed by the lens elements 117. Notwithstanding this complex arrangement, MMAL is used because its range of numerical aperture change is large.

Figure 12:
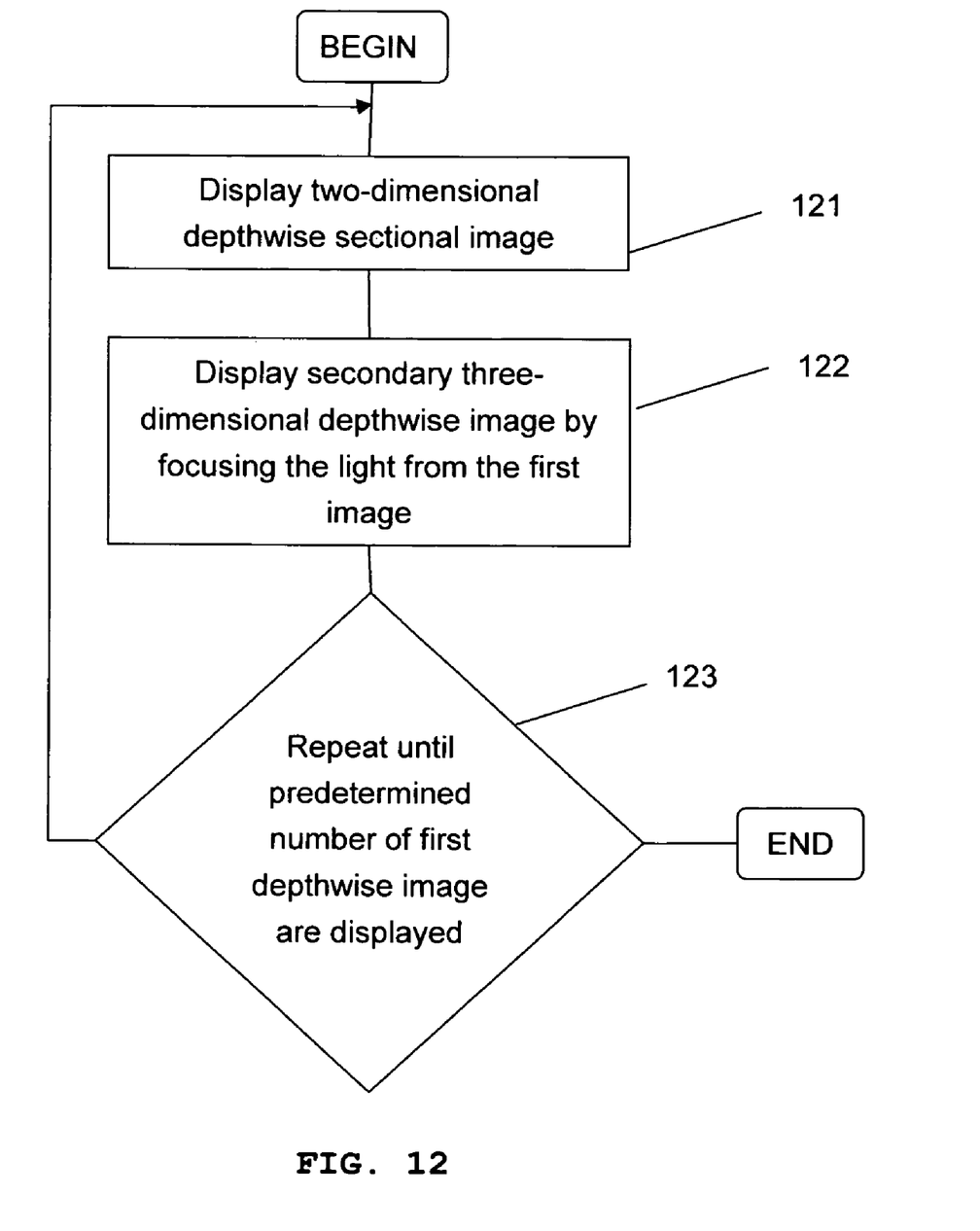
FIG. 12 is a flow diagram showing a three-dimensional display method of the present invention.

FIG. 12 shows a three-dimensional display method according to the invention. In step 121, a depthwise sectional image is displayed in two-dimension. Then in step 122, an all-in-focus image with depth information is displayed by receiving light from the displayed depthwise sectional image and focusing the light according to the depth of the depthwise sectional image. In step 123, steps 121 and 122 are repeated for a predetermined number of the depthwise sectional images within a unit time. The predetermined number of the depthwise sectional images forms an all-in-focus image, and each of the depthwise sectional images represents the portion of the image having the same image depth. The displayed images with depth information form an all-in-focus image with depth information that looks three-dimensional for a viewer. The focusing speed in the step of displaying the all-in-focus image with depth information is at least equal to the product of the persistent rate of the human eye and the number of depths. In the step of displaying the all-in-focus image with depth information, the light received from the displayed depthwise sectional image is reflected.

The step of displaying the all-in-focus image with depth information, 122 is performed with a MMAL.

While the invention has been shown and described with reference to different embodiments thereof, it will be appreciated by those skills in the art that variations in form, detail, compositions and operation may be made without departing from the spirit and scope of the invention as defined by the accompanying claims.

What is claimed is:

1. An image-guide microsurgery system comprising:
   a three-dimensional microscopic imaging device comprising:
   a) a lens system having an objective lens, and a variable focal length micromirror array lens (MMAL) optically coupled to the objective lens, wherein the variable focal length MMAL comprises a plurality of micromirrors, wherein each micromirror is independently controlled to change focal length of the variable focal length MMAL and compensates aberration of the three-dimensional microscopic imaging device;
   b) an imaging unit, optically coupled to the lens system, configured to receive the focused object image from the lens system and to sense the focused object image; and
   c) an image processing unit, communicatively coupled to the imaging unit, configured to process the object image sensed by the imaging unit and to generate all-in-focus image with depth information;
   and a three-dimensional display device, wherein three-dimensional display forms three-dimensional images by using all-in-focus image with depth information.

2. The three-dimensional microscopic imaging device of claim 1, wherein the lens system with variable focal length MMAL further comprises an auxiliary lens or group of lenses to change the field of view and the image resolution.

3. The three-dimensional microscopic imaging device of claim 1, further comprising one or more auxiliary lenses for increasing the numerical aperture of the imaging system.

4. The three-dimensional microscopic imaging device of claim 1, wherein the lens system with variable focal length MMAL further comprises another variable focal length MMAL for variable magnification of the object.

5. The three-dimensional microscopic imaging device of claim 1, wherein the image processing unit generates all-in-focus image with depth information from the two-dimensional images with depth information.

6. The three-dimensional microscopic imaging device of claim 1, wherein the variable focal length MMAL is an adaptive optical component compensating the aberration of the system.

7. The three-dimensional display device of claim 1 comprising:
   a two-dimensional display displaying a depthwise sectional image; and
   a variable focal length MMAL receiving light from the two-dimensional display and forming a three-dimensional image.

8. The three-dimensional display of claim 7, wherein the three-dimensional display forms three-dimensional image from all-in-focus image with depth information.

9. The three-dimensional display device of claim 8, wherein the all-in-focus image comprises corresponding depthwise images, in which each of the depthwise images represents the portion of the all-in-focus image having the same image depth.

10. The three-dimensional display devices of claim 7, wherein the two-dimensional display shows one depthwise sectional image at a time with corresponding depth information.

11. The three-dimensional display device of claim 7, further comprising a beam splitter positioned in the path of light between the two-dimensional display and the variable focal length MMAL.

12. The three-dimensional display device of claim 7, wherein the variable focal length MMAL is positioned so that the path of the light reflected by the variable focal length MMAL is not blocked by the two-dimensional display.

13. The three-dimensional display device of claim 7, further comprising an auxiliary lens to increase display size of the three-dimensional display.

14. The three-dimensional display device of claim 7, wherein the focal length of the variable focal length MMAL can be fixed to display two-dimensional information.

15. The three-dimensional display device of claim 7, wherein an image of an object is divided into sectional images along the depth of the object, and each sectional image is focused at the depth of the sectional image so that image focused from the sectional images looks three-dimensional to a viewer.

* * * * *